United States Patent
Sharma et al.

(10) Patent No.: US 10,162,932 B2
(45) Date of Patent: Dec. 25, 2018

(54) METHOD AND SYSTEM FOR MULTI-SCALE ANATOMICAL AND FUNCTIONAL MODELING OF CORONARY CIRCULATION

(71) Applicants: Puneet Sharma, Rahway, NJ (US);
Lucian Mihai Itu, Princeton, NJ (US);
Bogdan Georgescu, Plainsboro, NJ (US); Viorel Mihalef, Keasbey, NJ (US); Ali Kamen, Skillman, NJ (US);
Dorin Comaniciu, Princeton Junction, NJ (US)

(72) Inventors: Puneet Sharma, Rahway, NJ (US);
Lucian Mihai Itu, Princeton, NJ (US);
Bogdan Georgescu, Plainsboro, NJ (US); Viorel Mihalef, Keasbey, NJ (US); Ali Kamen, Skillman, NJ (US);
Dorin Comaniciu, Princeton Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 901 days.

(21) Appl. No.: 13/672,781

(22) Filed: Nov. 9, 2012

(65) Prior Publication Data
US 2013/0132054 A1 May 23, 2013

Related U.S. Application Data

(60) Provisional application No. 61/557,935, filed on Nov. 10, 2011.

(51) Int. Cl.
*G06F 19/12* (2011.01)
*G16H 50/50* (2018.01)
(Continued)

(52) U.S. Cl.
CPC .............. *G06F 19/12* (2013.01); *G06F 19/00* (2013.01); *G16H 50/50* (2018.01); *G06F 19/321* (2013.01); *G16H 50/30* (2018.01)

(58) Field of Classification Search
CPC .............. G06F 19/3437; G06F 17/5009; G06F 19/345; G06T 2207/30101;
(Continued)

(56) References Cited

U.S. PATENT DOCUMENTS

| | | |
|---|---|---|
| 7,860,290 B2 | 12/2010 | Gulsun et al. |
| 7,953,266 B2 | 5/2011 | Gulsun et al. |

(Continued)

FOREIGN PATENT DOCUMENTS

| | | |
|---|---|---|
| JP | 2009519801 | 5/2009 |
| WO | 2009064715 A1 | 5/2009 |

(Continued)

OTHER PUBLICATIONS

Algranati, D., Mechanisms of myocardium-coronary vessel interaction, American Journal of Physiology: Heart and Circulatory Physiology, Mar. 2010, 298(3) published online Dec. 2009.*

(Continued)

*Primary Examiner* — Brian S Cook (57) ABSTRACT

A method and system for multi-scale anatomical and functional modeling of coronary circulation is disclosed. A patient-specific anatomical model of coronary arteries and the heart is generated from medical image data of a patient. A multi-scale functional model of coronary circulation is generated based on the patient-specific anatomical model. Blood flow is simulated in at least one stenosis region of at least one coronary artery using the multi-scale function model of coronary circulation. Hemodynamic quantities, such as fractional flow reserve (FFR), are computed to determine a functional assessment of the stenosis, and (Continued)

virtual intervention simulations are performed using the multi-scale function model of coronary circulation for decision support and intervention planning.

43 Claims, 8 Drawing Sheets

(51) Int. Cl.
  *G06F 19/00* (2018.01)
  *G16H 50/30* (2018.01)
(58) Field of Classification Search
  CPC ....... G06T 2207/30048; G06T 2210/24; G06T 7/0083; G06T 2207/10076; G06T 7/0093; G06K 9/342
  USPC .......................................... 703/11, 9; 702/19
  See application file for complete search history.

(56) References Cited

U.S. PATENT DOCUMENTS

| | | | |
|---|---|---|---|
| 8,098,918 B2 | 1/2012 | Zheng et al. | |
| 8,157,742 B2 | 4/2012 | Taylor | |
| 8,386,188 B2 | 2/2013 | Taylor et al. | |
| 2005/0249717 A1 | 11/2005 | Burgard et al. | |
| 2010/0007760 A1 | 1/2010 | Suzuki et al. | |
| 2010/0017171 A1 | 1/2010 | Spilker et al. | |
| 2010/0067760 A1* | 3/2010 | Zhang et al. | 382/130 |
| 2010/0070249 A1* | 3/2010 | Ionasec et al. | 703/2 |
| 2010/0239148 A1 | 9/2010 | Zheng et al. | |
| 2010/0241404 A1 | 9/2010 | Taylor | |
| 2011/0060576 A1 | 3/2011 | Sharma | |
| 2011/0071404 A1 | 3/2011 | Schmitt et al. | |
| 2011/0093243 A1 | 4/2011 | Tawhai | |
| 2011/0224542 A1 | 9/2011 | Mittal et al. | |
| 2011/0270051 A1* | 11/2011 | Naghavi et al. | 600/301 |
| 2012/0022843 A1 | 1/2012 | Ionasec et al. | |
| 2012/0041301 A1 | 2/2012 | Redel | |
| 2012/0041739 A1* | 2/2012 | Taylor | 703/11 |
| 2012/0072190 A1 | 3/2012 | Sharma et al. | |
| 2012/0121151 A1 | 5/2012 | Bernhardt et al. | |
| 2012/0203530 A1 | 8/2012 | Sharma et al. | |
| 2014/0249791 A1 | 9/2014 | Taylor | |

FOREIGN PATENT DOCUMENTS

| | | |
|---|---|---|
| WO | 2011038044 A2 | 3/2011 |
| WO | 2012021307 | 2/2012 |

OTHER PUBLICATIONS

Holzapfel, G.A., A Layer-Specific Three-Dimensional Model for the Simulation of Balloon Angioplasty using Magnetic Resonance Imaging and Mechanical Testing, Annals of Biomedical vol. 30, pp. 753-767, 2002.*
Passerini, T., Computational hemodynamics of the cerebral circulation: multiscale modeling from the circle of Willis to cerebral aneurysms, Politecnico Di Milano, 2009.*
Liu, B., Tang, D., Computer Simulations of Atherosclerotic Plaque Growth in Coronary Arteries, Mol Cell Biomech, Dec. 2010; 7(4): 193-202.*
Stone, P.H., Effect of Endothelial Shear Stress on the Progression of Coronary Artery Disease, Vascular Remodeling, and In-Stent Restenosis in Humans: In Vivo 6-Month Follow-up Study, 2003, DOI: 10.1161/01.CIR.0000080882.35274.AD.*
Davis, P.F., Hemodynamic Shear Stress and the Endothelium in Cardiovascular Pathophysiology, Nat Clin Cardiovascular Med. Jan. 2009; 6(1): 16-26. Doi:10.1038/ncpcardio1397.*
Martinez-Lemus, L.A., The Plastic Nature of the Vascular Wall: A Continuum of Remodeling Events Contributing to Control of Arteriolar Diameterand Structure, Physiology 24: 45-57, 2008; doi:10.1152/physiol.00029.2008.*
Passerini, T., A 3D/1 D geometrical multiscale model of cerebral vasculature, J. Eng. Math. (2009) 64:319-330 DOI 10.1007/s10665-009-9281-3.*
Chiu, J., Chien, S., Effects of Disturbed Flow on Vascular Endothelium: Pathophysiological Basis and Clinical Perspectives, Physiol Rev. Jan. 2011; 91(1):. doi:10.1152/physrev.00047.2009.*
NIH_2009 (Open Problems in Computational Vascular Biomechanics: Hemodynamics and Arterial Wall Mechanics, Comput Methods Appl Mech Eng. Sep. 15, 2009; 198 (45-46): 3514-3523. Doi:10.1016/j.cma. 2009.02.004).*
Torsion Defined Archived Wikipedia dated May 14, 2011 http://en.wikipedia.org/w/index.php?title=Torsion_(mechanics)&oldid=429097889 teaches torsion.*
Deformation Defined Archived Wikipedia dated May 22, 2011 http://en.wikipedia.org/w/index.php?title=Deformation_(mechanics)&oldid=430416221 Teaches deformation.*
Roylance,D., Mechanical Properties of Materials, 2008 teaches mechanical properties of materials.*
PCT International Search Report dated Mar. 6, 2013 corresponding to PCT International Application No. PCT/US2012/064604 filed Nov. 12, 2012 (10 pages).
Olufsen et al., "Numerical Simulation and Experimental Validation of Blood Flow in Arteries with Structure-Tree Outflow Conditions", Annals of Biomedical Engineering, vol. 28, pp. 1281-1299, 2000.
Stergiopulos et al., "Total Arterial Inertance as the Fourth Element of the Windkessel Model", Am. J. Physiol., H81-H88, 1999.
H.J. Kim et al., Patient specific modeling of blood flow and pressure in human coronary arteries, Annals of Biomedical Engineering, Oct. 31, 2010, pp. 3195-3209, vol. 38, No. 10.
Luca Formaggia et al., Multiscale modeling of the circulatory system: A preliminary analysis, Computing and visualization in science, Dec. 31, 1999, pp. 75-83.
John F Ladisa et al., Alterations in regional vascular geometry produced by theoretical stent, BioMedical Engineering Online 20065:40, Jun. 16, 2016, pp. 1-16.
Office Action in corresponding Japanese Patent Application No. 2014-541362 dated Dec. 7, 2015.
Office Action in corresponding Chinese Patent Application No. 2012800666658.1 dated Mar. 1, 2016.
Chiu, Jeng-Jiann et al., "Effects of disturbed flow on vascular endothelium: Pathophysiological basis and clinical perspectives", vol. 91, pp. 327-387, 2011, http://physrev.physiology.org/ (by 10.220.33.2 on Oct. 14, 2016 last download).
Tardy Y. et al., "Shear stress gradients remodel endothelial monolayers in vitro via cell proliferation-migration-loss cycle", Arteriosclerosis, Thrombosis and Vascular Biology, vol. 17, No. 11, pp. 3102-3106, Originally publishes Nov. 1, 1997 / Nov. 1, 1997.
Silva Jonathan R et al: "A multiscale model linking ion-channel molecular dynamics and electrostatics to the cardiac action potential", Proceedings National Academy of Sciences PNAS, vol. 106, No. 27, pp. 11102-11106.
Dur Onur et al: "Computer-Aided Patient-Specific Coronary Artery Graft Design Improvements Using CFD Coupled Shape Optimizer", Cardiovascular Engineering and Technology, vol. 2, No. 1, pp. 35-47.
Hand P E et al: "Adaptive multiscale model for simulatinq cardiac conduction", Proceedings National Academy of Sciences PNAS, vol. 107, No. 33.
Laganá Katia et al: "Multiscale modeling of the cardiovascular system: application to the study of pulmonary and coronary perfusions in the univentricular circulation", Journal of Biomechanics, Pergamon Press, New York, NY, US, vol. 38, No. 5, pp. 1129-1141.
Mihalef Viorel et al: "Patient-specific modelling of whole heart anatomy, dynamics and haemodynamics from four-dimensional cardiac CT images." Interface Focus, vol. 1, No. 3, pp. 286-296.
Spycher Philipp R et al: "Dual, Site-Specific Modification of Antibodies by Using Solid-Phase Immobilized Microbial Transglutaminase", Chembiochem—A European Journal of Chemical Biology, vol. 18, No. 19, pp. 1923-1927.
European Office Action dated Oct. 20, 2017 in corresponding EP application No. 12795185.3.

* cited by examiner

METHOD AND SYSTEM FOR MULTI-SCALE ANATOMICAL AND FUNCTIONAL MODELING OF CORONARY CIRCULATION

This application claims the benefit of U.S. Provisional Application No. 61/557,935, filed Nov. 10, 2011, the disclosure of which is herein incorporated by reference.

BACKGROUND OF THE INVENTION

The present invention relates to anatomical and functional modeling of coronary circulation, and more particularly, to multi-scale anatomical and functional modeling of coronary circulation for coronary artery disease diagnosis and intervention planning.

Cardiovascular disease (CVD) is the leading cause of deaths worldwide. Among various CVDs, coronary artery disease (CAD) accounts for nearly fifty percent of those deaths. Despite significant improvements in medical imaging and other diagnostic modalities, the increase in premature morbidity and mortality for CAD patients is still very high. One reason for this is the lack of accurate in-vivo and in-vitro patient-specific estimates for diagnosis and progression of the disease. For example, in the case of coronary stenosis, accurate estimates of the anatomy (i.e., the amount of narrowing in the coronary) as seen in diagnostic images can vastly underestimate or overestimate the severity of the blockage. For a functional assessment of such a blockage, it is important to incorporate multi-faceted information from the hemodynamics and cellular mechanisms from multiple scales. Incorporating such multi-scale information in a complex model has been difficult in the past due to high computational demands.

BRIEF SUMMARY OF THE INVENTION

The present invention provides a method and system for multi-scale anatomical and functional modeling of coronary circulation. Embodiments of the present invention efficiently incorporate full-order and reduced order sub-models of the coronary circulation anatomy. Embodiments of the present invention provide patient-specific multi-scale computational models with high predictive power for coronary circulation in healthy and diseased vessels. Embodiments of the present invention further provide virtual intervention based planning to improve the clinical management of coronary artery disease by leveraging the computational models to create specific to create specific therapeutic interventions.

In one embodiment of the present invention, a patient-specific anatomical model of coronary arteries and the heart is generated from medical image data of a patient. A multi-scale functional model of coronary circulation is generated based on the patient-specific anatomical model. Blood flow is simulated in at least one stenosis region of at least one coronary artery using the multi-scale function model of coronary circulation.

These and other advantages of the invention will be apparent to those of ordinary skill in the art by reference to the following detailed description and the accompanying drawings.

DETAILED DESCRIPTION

The present invention relates to multi-scale anatomical and functional modeling of coronary circulation using medical image data. Embodiments of the present invention are described herein to give a visual understanding of the methods for modeling coronary circulation. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Embodiments of the present invention provide patient-specific multi-scale computational models with high predictive power for coronary circulation in healthy and diseased vessels. Such computational models are implemented with the following components: comprehensive modeling of the anatomical, hemodynamical, and cellular phenomena in the coronary circulation; efficient multi-scale coupling with state-of-the-art heart models for advanced patient-specific computations; and determination of functional parameters and hemodynamic quantities, such as fractional flow reserve (FFR), coronary flow reserve (CFR), lesion severity index, etc., for diagnosis and assessment of the severity of coronary stenosis. Embodiments of the present invention further provide virtual intervention based planning to improve the clinical management of coronary artery disease by leveraging the computational models to create specific to create specific therapeutic interventions. Such virtual intervention planning is implemented using simulation based methods for intervention planning (virtual stenting, angioplasty, and Coronary Artery Bypass Graft (CABG)) using the computational models. Such embodiments result in a predictive comprehensive multi-scale model, which can be used not only for analyzing anatomical and functional aspects of coronary artery disease, but also for improved clinical management both for diagnosis and intervention planning.

Figure 1A:
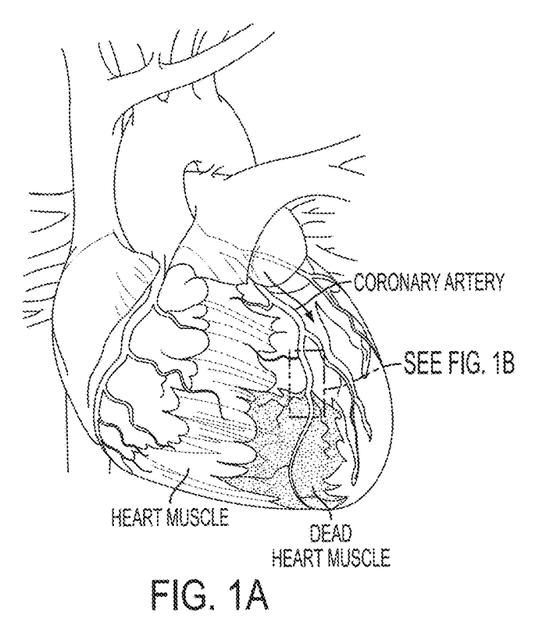
FIG. 1 is a graphic illustration of coronary artery disease.
Figure 1B:
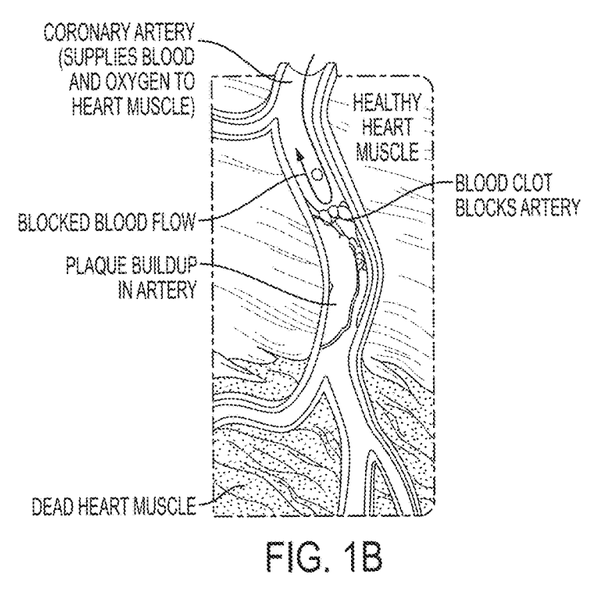

FIG. 1 is a graphic illustration of coronary artery disease. As shown in FIG. 1, coronary artery disease is characterized by narrowing of the blood vessels due to the buildup of plaque inside the coronaries, which results in a reduced oxygen supply to the myocardium. Over time, the consequences can be severe, resulting in angina, myocardial infarction, stroke, or death.

The functional importance of coronary artery disease cannot be determined merely by observing the narrowing of the blood vessels and is related to different blood flow properties like flow rate and pressure. Current clinical practice involves invasive measurements for the proper evaluation of these quantities. In advantageous embodiments of the present invention, the risks associated with these interventions can be avoided by first acquiring detailed information on the geometry of coronary arterial trees through different imaging techniques and then by performing blood flow computations on models representing the patient-specific geometry. Further these models not only allow one to avoid invasive measurements, but also to improve treatment plans by simulating different scenarios (angioplasty, stenting, bypass procedures) and hence to improve patient outcome.

Recently, Computational Fluid Dynamics (CFD) based blood flow simulations have been reported and validated against patient-specific data (acquired through ultrasound, MRI, CT, etc.). Such models are well suited for organ level analysis, but fail to account for the complex multi-scale phenomenon that is crucial for obtaining comprehensive predictive models (at every scale) for intervention planning. Another major challenge when developing an application for the clinical setting is to reduce the computational complexity, so that the results can be obtained in a reasonable amount of time and can be applied efficiently in clinical practice.

Since the coronary vessels supply the myocardium, they are strongly coupled to the heart and its mechanical action performed especially on the microvascular vessels. Hence in order to perform a physiologically accurate computation, it is crucial to precisely embed the effects exercised by the heart on the coronary vessels. Furthermore, the development of coronary artery disease is related to phenomena taking place at cell-level (at the endothelial layer of blood vessels). The incorporation of cell-level models allows tracking the development of plaque deposits and their gradually increasing effect on the microvascular beds supplied by the corresponding epicardial artery. This shows that a reliable evaluation of the functional importance of diseased vessels requires a complex setup, which cannot be obtained solely through blood flow computations, but the model described herein efficiently takes into account all aspects.

Another aspect is that in order to increase the productivity of these models and to be able to diagnose an increased number of patients, the execution time of multi-scale models has to be optimized. To address this, efficient coupling strategies are needed, which drastically reduce the execution time, without compromising on the model physics. This problem is addressed in the embodiments of the present invention by efficiently using and coupling full-order and reduced-order models by balancing the model complexity versus execution time.

After determining the functional significance of epicardial stenosis, the anatomical and functional models will be used to simulate the effect of different interventions, which may improve the health state of the patient. Balloon inflation can be modeled by virtually reducing the obstruction from the stenosis. Virtual stent implantation (with stents from different manufacturers), followed by performing the coupled flow analysis will enable the analysis of the effects on wave propagation inside the arterial tree, and its impact on the hemodynamic variables. In some cases, coronary artery bypass grafting (CABG) procedure is typically performed. The introduction of such adjacent vessels, using various start and end points, can also be simulated inside these models; hence the most suitable option can be determined prior to the intervention.

Figure 2:
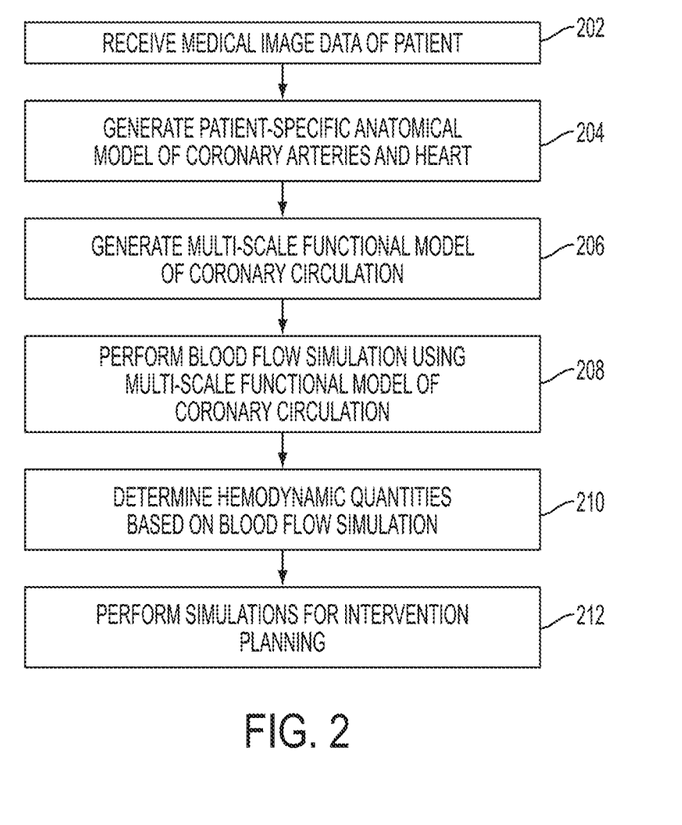
FIG. 2 illustrates a method of modeling coronary circulation, assessment of coronary artery disease, and intervention planning according to an embodiment of the present invention.

FIG. 2 illustrates a method of modeling coronary circulation, assessment of coronary artery disease, and intervention planning according to an embodiment of the present invention.

At step 202, medical image data of a patient is received. Medical image data from one or multiple imaging modalities can be received. For example, the medical image data can include, computed tomography (CT), Dyna CT, magnetic resonance (MR), Angiography, Ultrasound, Single Photon Emission computed Tomography (SPECT), and any other type of medical imaging modality. The medical image data can be 2D, 3D or 4D (3D+time) medical image data. The medical image data can be received directly from one or more image acquisition devices, such as a CT scanner, MR scanner, Angiography scanner, Ultrasound device, etc., or the medical image data may be received by loading previously stored medical image data for a patient.

At step 204, a patient-specific anatomical model of the coronary arteries and the heart is generated from the medical image data. In an advantageous implementation, the patient-specific anatomical model includes a 4D (3D +time) a geometric model of the coronary arteries generated using the 4D medical image data. In order to generate the patient-specific anatomical model of the coronary arteries, the coronary arteries are segmented in each frame of the 4D image data. The coronary arteries can be segmented in each frame of the medical image data using any coronary artery segmentation method. For example, the coronary arteries can be segmented in a CT volume using the method described United States Published Patent Application No. 2010/0067760, which is incorporated herein by reference. A geometric surface model is then generated for the segmented coronary arteries of interest in each frame. For example, methods for anatomical modeling of the coronary arteries are described in U.S. Pat. Nos. 7,860,290 and 7,953,266, both of which are incorporated herein by reference. This results in an anatomical model of the coronary arteries that shows the anatomy of the coronary arteries changing over time.

In an advantageous embodiment, the patient-specific anatomical model also includes a patient-specific 4D anatomical model of the heart that is generated from the 4D image data. The 4D anatomical heart model is a multi-component model having multiple cardiac components, including as the chambers (left ventricle, left atrium, right ventricle, and right atrium), the heart valves (aortic valve, mitral valve, tricuspid valve, and pulmonary valve), and the aorta. Such a comprehensive model of the heart is used to capture a large variety of morphological, functional, and pathological variations. A modular and hierarchical approach can be used to reduce anatomical complexity and facilitate an effective and flexible estimation of individual anatomies. The 4D anatomical heart model can be generated by generating individual models of each heart component, for example using marginal space learning (MSL), and then integrating the heart component models by establishing mesh point correspondence. Additional details regarding generation of such a 4D patient-specific heart model are described in United States Published Patent Application No. 2012/0022843, which is incorporated herein by reference.

At step 206, a multi-scale functional model of coronary circulation is generated. One of the major difficulties regarding the precise modeling of the human cardiovascular system is the fact that is represents a closed circuit with a high degree of interdependence between the individual components. The blood flow characteristics in a certain segment of the system (the local hemodynamics) are closely related to the global dynamics of the system. Studying the local blood flow is important, since certain pathologies, like the local thickening of the blood vessel or the formation of a stenosis, are strongly influenced by the local hemodynamics. On the other hand, certain local changes, like the modification of the vascular lumen, may lead to a global redistribution of blood flow, triggering some compensatory mechanism which assures a high enough flow rate in the distal part of the affected vessel. 3D or full-scale blood flow computations are computationally expensive and can only be performed for a reduced number of vessels. Both the reciprocal influence between the systemic or the global hemodynamics and the local hemodynamics, and the high computational requirements of 3D computations, have led to the concept of geometrical multi-scale modeling of blood flow, which is used herein in order to analyze the coronary circulation.

Accordingly, in an advantageous embodiment of the present invention, only local regions of interest inside the coronary arterial tree, e.g., segments which contain narrowing plaque deposits are segmented using full 3D models, while the rest of the circulation is represented through reduced-order models (1D models for the large arteries and lumped models for the small arteries and microvasculature). Reduced-order models produce reliable results in terms of pressure and flow rate waveforms (1D models), correctly take into account the effect of distal vessels and of the microvasculature (lumped models), and lead to execution times which are more than two orders of magnitude smaller than the corresponding 3D computations. Alternatively, the entire computation may be implemented on a 3D model.

Figure 3:
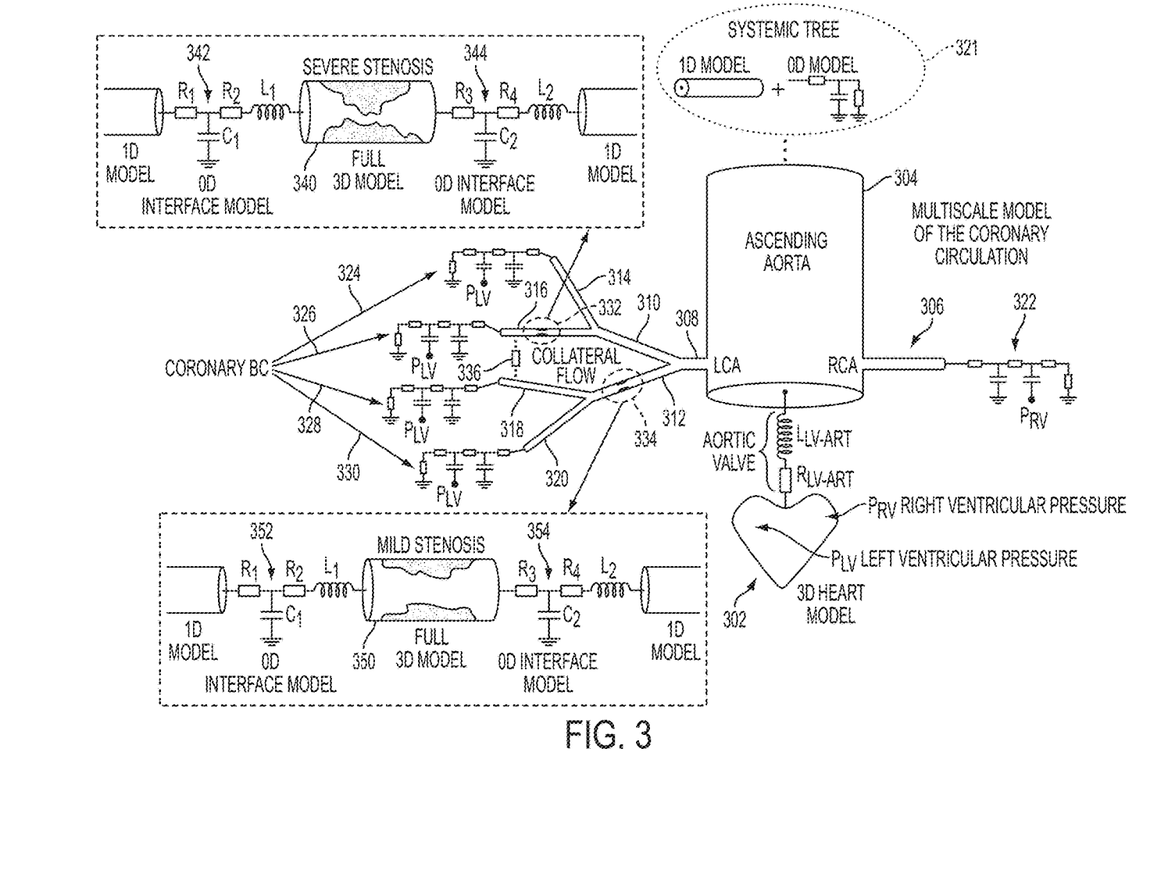
FIG. 3 illustrates an overview of the multi-scale modeling approach according to an embodiment of the present invention.

FIG. 3 illustrates an overview of the multi-scale modeling approach according to an embodiment of the present invention. As shown in FIG. 3, a heart model 302 is coupled at the root of the aorta. The heart model 302 may be implemented as a full 3D heart model or may be implemented as a lumped model parameterized through patient-specific data. The aorta and the large arteries (e.g., the left coronary artery (LCA), right coronary artery (RCA), etc.) are represented as 1D blood flow models 304, 306, 308, 310, 312, 314, 316, 318, and 320 since these 1D blood flow models 304-318 produce reliable results in terms of pressure and flow rate values and take into account wave propagation phenomena. All microvascular beds will be simulated through lumped parameter models 322, 324, 326, 328, and 330 which account for the resistance applied to the blood flow and for the compliance of the distal vessels. For the coronary arterial tree, the flow in the large (epicardial) vessels is computed through 1D models in a systemic tree model 321. The stenosis segments 332 and 334 (i.e., areas in the vessels were stenosis or narrowing is detected) cannot be simulated using the 1D blood flow models since there is a high variation in cross-sectional area and the shape of the stenosis influences the blood flow behavior and especially the trans-stenotic pressure drop which plays a major role in the assessment of the functional importance of such a stenosis. The coronary vascular bed is modeled through lumped parameter models 324, 326, 328, and 330, which are adapted to the coronary circulation in the sense that they take into account the effects of the myocardial contraction during systole.

Since execution time is crucial, according to an advantageous implementation, rigid wall 3D models 340 and 350 can be used to represent the stenosis regions 332 and 334 instead of 3D fluid-structure interaction (FSI) whose execution times are more than two times higher. This aspect does not influence the overall results, since the elasticity in the stenosis regions 332 and 334 is not important, but in order to correctly represent the wave propagation phenomena inside the coronary tree, 0D interface models 342, 344, 352, and 354 are included at the interfaces between the compliant 1D models and the rigid 3D models. These interface models concentrate the compliance of the 3D segments at its interfaces. One further aspect which is very important in the coronary circulation, and which contributes to the large discordance between morphological and functional importance of a stenosis is the presence of collateral flow which can render a morphologically important stenosis into a functionally insignificant one. Depending on the patient specific vessel morphology, the collateral flow 336 can be modeled both through anastomotic large vessels (with 1D models) or through microvascular vessels which supply the affected region with blood (modeled through lumped elements as in FIG. 3).

Lumped Models for the Small Arteries and Microvasculature

The lumped or 0D models 322-330 of the microvasculature are based on the analogy between electricity and hydraulics and eliminate the spatial dependency of the independent variables by concentrating the physiological properties of the small vessels into lumped elements: resistance, compliance and inertance. The coronary bed requires a special treatment since the microvascular vessels are the ones most influenced by a myocardial contraction, whose effect varies between epicardium and endocardium. Three different mechanisms can be used to explain the observed flow rate waveform inside the coronary tree: varying elasticity, shortening-induced intracellular pressure and cavity induced extracellular pressure. In an advantageous implementation, a combination of the second and third mechanisms are used to model the effect of the myocardial contraction of the coronary flow, whereas the varying elasticity rather protects the vessels against the action of the other two mechanisms. Thus, during systole, an external pressure acts on the coronary vessels which is higher in the subendocardium and lower in the subepicardium and which can be determined from the left and right ventricular pressures. The epicardial vessels, which run on the surface of the myocardium are not affected by these contractions. In the multi-scale perspective, regular 3-element Windkessel models can be used at the termination sites of vessels which do not belong to the coronary tree. The values of the resistances and compliances are determined by taking the average pressure and flow rate values and by adapting the resistance values in order to avoid non-physiological reflections.

Detailed 3D Anatomical Model for the Epicardial Stenosis Segment

The detailed 3D blood flow computation 340 and 350 in each stenotic region 332 and 334 is based on the numerical solution of the incompressible Navier-Stokes equations in a rigid domain. No-slip boundary conditions are enforced at the vessel walls and the inflow and outflow boundary conditions are determined by an explicit/implicit coupling with the proximal and distal 1D segments. In an advantageous implementation, the 3D model 340 and 350 not only determines values of local parameters of interest like wall shear stress, but for stenotic regions, it also computes pressure drops for the detailed shape of the stenosis.

1D Model for the Aorta and the Segments Proximal and Distal to the Stenosis Regions; and Structured Tree Model for the Vascular Tree The 1D models 304-320 use a series of simplifying assumptions in order to convert a 3D domain into a 1D domain along the length of the longitudinal axes. Such 1D models can be described by a system of quasilinear first order partial differential equations. An advantageous aspect of these models is the fact they take into consideration the compliance of the vessels, which allows for the description of wave phenomena which appear in the cardiovascular system. The dependent variables of these models are the lumen area, the flow rate, and the average pressure along the longitudinal axis (typically a network of compliant blood vessels is considered). 1D models can for example be used to study the effect of geometric tapering or local stiffening of an artery on the propagation of flow rate and pressure waves. 1D models are very useful when determining the characteristics of the flow rate and pressure waves inside the cardio-vascular system. These waves are generated by the interaction between the blood flow and the vessel walls, which have certain compliance, and depend on the elastic characteristics of the vessels. There are various approach possibilities regarding these models. In the simplest case, the mechanical properties of the blood vessel are described by an algebraic relation between average pressure and the radius of the vessel. In more complex situations, other properties like visco-elasticity or wall inertia may be considered. In an advantageous embodiment of the present invention, the relationship between pressure and vessel radius is given by a differential equation. Blood flow computations using 1D models have been shown to produce good results in terms of pressure and flow rate (velocity) values and have the advantage of a reduced computational effort. Hence, when blood vessel anatomy is regular (e.g., cylindrical) and there is no need for computing local values like wall shear stress or oscillatory shear index, such 1D models can be used in order to reduce the computational time but also to study the wave propagation phenomena. These 1D models are used both before and after the stenotic segments, thus allowing a detailed spatial pressure and flow rate distribution in the whole coronary arterial tree to be determined. Further, the 1D models (which contain non-linear terms) can be linearized and exact analytic solutions can be obtained in the frequency domain. This way a structured tree model 321 can be obtained for the distal part of the arterial tree, which can be then lumped into impedance and applied as boundary condition at the outlet of the non-linear 1D model.

Lumped Models at the 1D-3D Coupling Interfaces 3D blood flow computations can be performed both with rigid and compliant walls (fluid structure interaction). The rigid wall computations are considerably faster and the elasticity is reduced in the stenotic regions (because of the plaque deposit but also because coronary vessels have a relatively small diameter characterized by an increased stiffness). Thus, the stenotic regions 332 and 334 are simulated with rigid walls and even if vascular compliance is often not relevant to the meaningfulness of 3D results by themselves, it is crucial in the multi-scale model, since it is the driving mechanism of pressure-wave propagation, which is of great interest in the whole coronary tree. Hence, the compliance of the stenotic segments has to be taken into account and this can be best done by introducing a 0D model 342, 344, 352, and 354 at the interface between the 1D and the 3D segments, which concentrates the compliance of the 3D segment. Pressure and flow rate wave propagation in the coronary tree is complex because of the influence of the myocardial contraction and has not been studied extensively up to date.

Even though a 0D model 342, 344, 352, and 354 is introduced at the interface between the 1D and 3D model, some difficulties still may arise at the coupling points in the multi-scale model. A proper coupling between 1D and 3D models is difficult to achieve, an aspect which is emphasized by the different mathematical nature of the models. The Navier-Stokes equations represent a system of partial differential equations which are parabolic from the velocities' perspective whereas the 1D models rely on hyperbolic partial differential equations. Under these conditions one has to assure that the mathematical problem is well posed and that the numerical results are of the desired accuracy. There are various possibilities which can be used to assure a proper coupling of the models: the so-called "do-nothing" approach (typically used for pressure boundary conditions) and the "Lagrange multiplier" approach (typically used for velocity-flow rate boundary conditions). By coupling the models, the global and the local behavior of blood can be determined, as well as the reciprocal influence between the local and global model.

Coronary Autoregulation and Hyperemia Modeling

Coronary autoregulation plays a major role in the adaptation of the coronary tree to arterosclerotic segments in the epicardial vessels. Autoregulation refers to the change in the microvascular resistance as a reaction to a change in the perfusion pressure and its role is to maintain a constant flow rate through the capillaries. This aspect refers to the normal or rest state of the body. Another type of regulation takes place at exercise or drug-induced hyperemia, when the microvascular resistance decreases to a minimum in order to allow a three to five-fold increase of the flow rate. Both of these aspects have to be taken into account inside a multi-scale model of the coronary tree.

Figure 4:
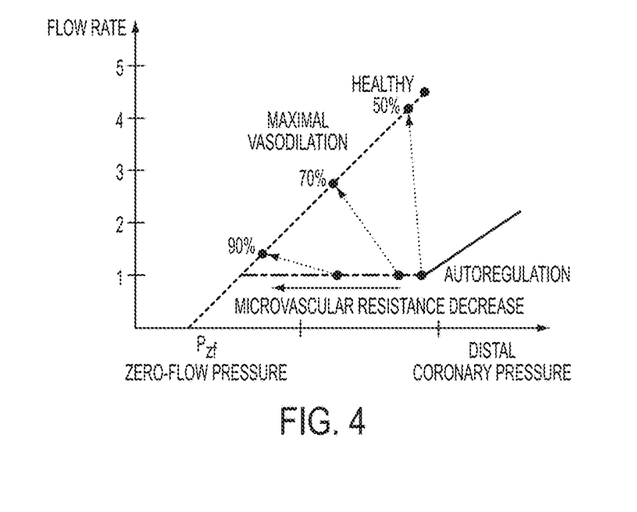
FIG. 4 is a graph illustrating coronary autoregulation.

FIG. 4 is a graph illustrating coronary autoregulation. Autoregulation takes place at rest state, i.e., with reduced heart rate and blood pressure, and for a stenosed vessel leads to a reduced microvascular resistance which compensates for the introduction of the flow-dependent stenosis resistance. An important aspect which influences the coronary flow in general and the autoregulation phenomenon in particular is the presence of collateral flow. These vessels, also called anastomotic channels, develop in the heart as an adaption to ischemia. They serve as conduit segments which bridge severe stenoses or connect a territory supplied by one epicardial coronary artery with that of another. Hence, collateral vessels represent an alternative source of blood supply to a certain part of the myocardium which is affected by coronary artery disease, and they can help to preserve myocardial function. There are two different types of collateral vessels: capillary size collaterals, in which smooth muscle cells are absent (they usually appear in the subendocardium) and larger, muscular collaterals, which develop from already existent arterioles (they usually appear in the epicardium). The second type of regulation is important in order to simulate the effect of a hyperemia inducing drug which is applied in clinical practice in order to determine the functional significance of a stenosis. In the presence of a stenosis the hyperemic flow of a stenosed segment can no longer reach the maximum values, which would have been obtained in case of a normal, healthy vessel. This is caused by the resistance introduced by the stenosis, which limits the maximum flow, since the microvascular resistance cannot decrease below its normal lower limit.

Cellular Models for Mechanobiology and Mechanotransduction

The predictive nature of the multi-scale coupled model of the coronary circulation is intrinsically linked to its coupling with cellular models. This makes it possible to track the initiation, and subsequent growth of coronary plaques and their effect on the overall circulation. It has been shown that blood flow induced wall shear stress in the coronary arteries not only effects plaque development, but is also linked to plaque rupture. The mechanism behind aspect this is generally explained by the role of the endothelial cells, which have been known to respond to hemodynamic forces. The shear stress exerted on the vessel wall is converted in a biochemical signal via the process of mechanotransduction. This ultimately results in specific changes in the vessel wall. The shear forces are exerted on the endothelium and modulate endothelial structure and function through the local mechanotransduction mechanisms. In an advantageous implementations, various analytical and mathematical models of mechanotransduction can be used and coupled with the organ level circulation model. This coupling is performed throughout the wall-shear stress value that is obtained from the hemodynamic computations and then passed as an input to the mechanotransduction model. Endothelial cells not only regulate the vascular tone, but also remodel the vascular wall in response to hemodynamic changes due to the stenosis which will be taken into account by the mechanotransduction models. This remodeling will have an effect on the organ level circulation model.

Reduced Order Model of the Heart

There are several parametric heart models, which are very useful in simulating different states of the body. Some of the most used are the varying elastance model and the single fiber model. These heart models can determine the pressure and the flow in the different heart chambers without considering a spatial model of the heart. Several parameters like contractility, stroke volume, time-to-maximum, dead volume, heart rate can be adapted in order to account for different states of the body and to personalize the model.

In an advantageous embodiment of the present invention, reduced-order heart models are extracted from full-order anatomical and hemodynamic models of the heart, and efficiently coupled them with the coronary circulation models. In particular, patient-specific advanced models of the heart morphology, dynamics, and hemodynamics generated from the received medical image data can be integrated. Physiological landmarks are explicitly represented in the extracted anatomical heart model and provide semantic associations to the underlying anatomy. The models are highly modular and can be customized depending on the application, and include anatomy and dynamics of the left and right ventricles, left and right atria, aorta, aortic valve, mitral valve, tricuspid valve, pulmonary valve and trunk, pulmonary veins, and superior/inferior vena cava. Advanced morphological and dynamical parameters are readily available and can be used to study the coupled function of the heart. Models can be personalized using various types of imaging modalities (e.g., CT, MRI, Ultrasound, etc.).

Recent developments in real-time full volume echocardiography create the opportunity to recover full 3D myocardial motion as well as volumetric color Doppler information. Dense myocardial motion provides critical information for personalization of the heart model, as well as in the study of moving coronary vessels. Multiple information sources, such as speckle patterns, image gradients, boundary detection, and motion prediction can be fused to achieve a fast and robust detection and dense tracking of the heart anatomy on 3D+t ultrasound data. Such echo-based estimated motion and mechanical parameters of the myocardium are sufficiently close to ground truth values. In an advantageous implementation, the availability of volumetric color Doppler velocity enables fast and non-invasive recovery of patient-specific blood flow information, which can be used as boundary conditions for subsequent CFD computations.

Figure 5:
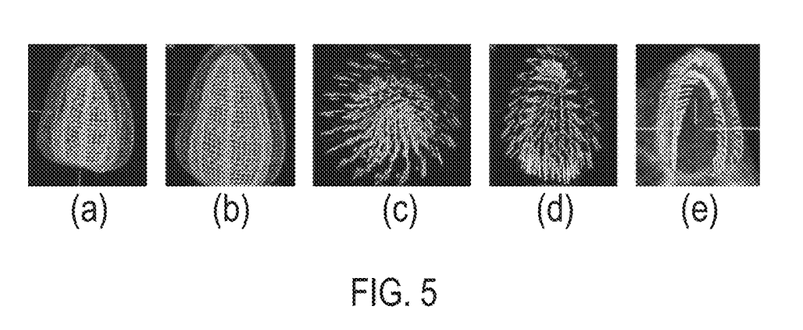
FIG. 5 illustrates estimation of myocardial mechanics from high frame rate volumetric ultrasound images.

FIG. 5 illustrates estimation of myocardial mechanics from high frame rate volumetric ultrasound images. As shown in FIG. 5, image (a) shows the myocardium at systole, image (b) shows the myocardium at diastole, images (c) and (d) show 3D dense motion vectors demonstrating the helical motion of the myocardium, and image (e) shows a projection of the endocardium and epicardium contours and the motion vectors onto the 4 chamber plane.

Figure 6:
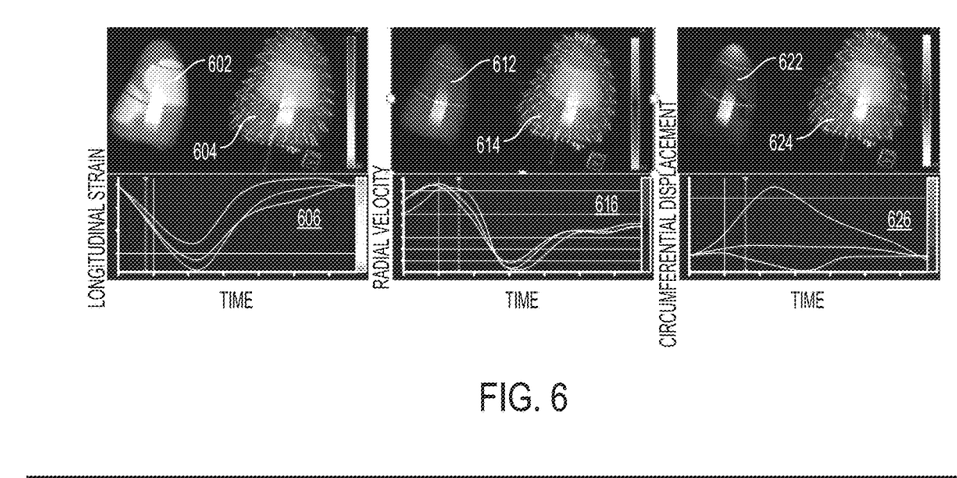
FIG. 6 illustrates estimation of left ventricle myocardial mechanics.

FIG. 6 illustrates estimation of left ventricle myocardial mechanics. As shown in image (a) of FIG. 6, 602 shows the estimated values of longitudinal strain mapped to the endocardial boundary, 604 shows the direction and magnitude of the dense velocity field, and 606 shows plots of estimated longitudinal strain versus time for the apical, mid, and basal regions. As shown in image (b) of FIG. 6, 612 shows the estimated values of radial velocity mapped to the endocardial boundary, 614 shows the direction and magnitude of the dense velocity field, and 616 shows plots of estimated radial velocity versus time for the apical, mid, and basal regions. As shown in image (c) of FIG. 6, 622 shows the estimated values of circumferential displacement mapped to the endocardial boundary, 624 shows the direction and magnitude of the dense velocity field, and 626 shows plots of estimated circumferential displacement versus time for the apical, mid, and basal regions.

Figure 7:
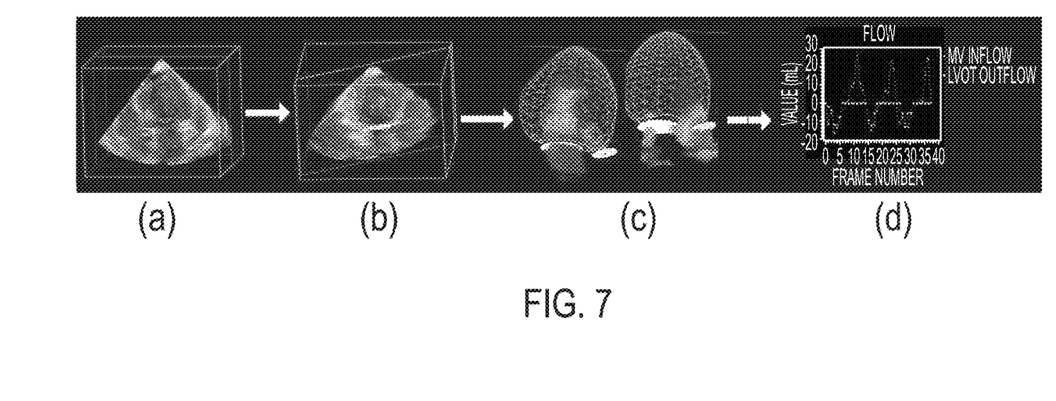
FIG. 7 illustrates automatic quantification of the volumetric flow.

FIG. 7 illustrates automatic quantification of the volumetric flow. Image (a) shows a volumetric b-mode and color ultrasound that is acquired for a patient. Image (b) shows automatic detection and tracking of the left ventricle, mitral valve (MV), and left ventricle outflow tract (LVOT) in the ultrasound. Image (c) shows flow sampling at the MV and LVOT tracked locations. Image (d) shows inflow/outflow quantification and de-aliasing.

Figure 8:
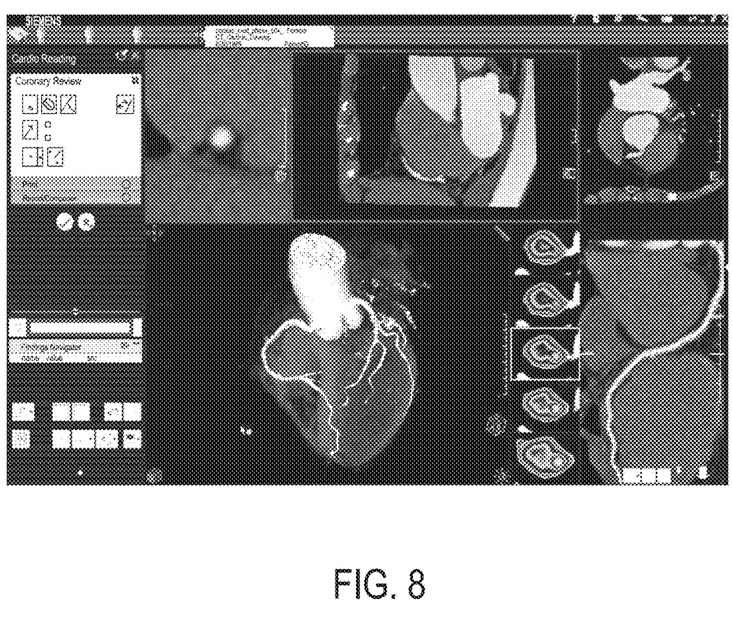
FIG. 8 illustrates exemplary medical image processing software for coronary vessel extraction and anatomical assessment of coronary stenosis.

In order to extract the coronary anatomy from the medical images, embodiments of the present invention can utilize existing coronary segmentation and centerline extraction algorithms. Such algorithms readily provide the coronary vessel centerline tree, together with a surface representation including the stenosis narrowing, which is then used for extracting the required anatomical data for the 3D and 1D computations. For example, the percent blockage of a stenosis can be detected and used to construct the 3D model of the stenosis region. FIG. 8 illustrates exemplary medical image processing software for coronary vessel extraction and anatomical assessment of coronary stenosis.

With recent advances in patient-specific 4-D anatomical modeling, High Performance Computing (HPC), and 3-D flow measurement techniques via imaging, it is possible to employ computational fluid dynamics (CFD) techniques for hemodynamic assessment and subsequent validation in cardio-vascular applications. While most previous approaches focused on a single cardiac component interacting with blood either rigidly or using fluid structure interaction (FSI) methods, embodiments of the present invention utilized CFD computations of whole heart blood flow using high-quality patient-specific heart models derived from 4D CT data. The 4D physiological models captured from the 4D CT have been used to provide proper constraints for the computations of the blood flow inside the heart. Additional details regarding patient-specific CFD computations using 4D heart models are described in United States Published Patent Application No. 2012/0022843, entitled "Method and System for Comprehensive Patient-Specific Modeling of the Heart", which is incorporated herein by reference.

Returning to FIG. 2, at step 208, blood flow computation is performed using the multi-scale functional model of coronary circulation. The blood flow is simulated in the 3D models of the stenosis regions of the coronary arteries using CFD with patient-specific boundary conditions. In particular, blood is modeled as a Newtonian fluid, and the velocity field is obtained by numerically solving the discretized Navier-Stokes equations (continuity and momentum equations) under the rigid wall assumption. The discretized Navier-Stokes equations are used to incrementally simulate velocity of blood flow and pressure within the coronary arteries over time. This computes the flow in all directions in the 3D model as a function of time. Additional details regarding CFD computations using discretized Navier-Stokes equations are described in United States Published Patent Application No. 2012/0022843, entitled "Method and System for Comprehensive Patient-Specific Modeling of the Heart", which is incorporated herein by reference. The patient-specific anatomy of the stenosis regions are also input to the CFD modeling in order to constrain the blood flow computations based on the patient-specific anatomy. Furthermore, the 3D computations of the stenosis regions are coupled with the 1D computations of the surrounding portions of the coronary arteries. The computations for the 1D models (e.g., for the coronary arteries and the aorta) compute the bulk flow rate going through the particular coronary branch (or aorta). The 1D computation can also be performed using Navier-Stokes equations. The 0D models (lump models) are mathematical abstractions of anatomical models and give output values based on an input condition.

In order to simulate blood flow the using the patient-specific multi-scale model, the multi-scale heart, coronary circulation, and cellular models must be efficiently coupled. Implicit coupling can be implemented between the left ventricle and the aorta. The inflow boundary condition for the systemic tree (321 of FIG. 3) is derived by coupling the aorta to the left ventricle of the heart. Thus, the cardiac output determined at the inlet of the aorta is determined not only by the heart model but also by the characteristics of the systemic tree to which it is coupled.

Effects of the myocardial contraction on the coronary circulation are estimated by using a full scale model of the heart. In particular, in an advantageous implementation, the full-scale model of the heart is used to determine the influence of the heart contractions on each of the epicardial coronary vessels. There is a major difference between the right and left side of the heart, but also locally more detailed variations can be taken into account. The 3D strain map extracted from the image data can be used for imposing these boundary conditions.

The pressures inside the left and right ventricles exert an extracellular pressure on the vessels. The amount of pressure depends on the location of the vessels, i.e., in the epicardium (low pressure) or endocardium (high pressure). This information can be used directly in the lumped parameter models of the coronary bed to account for the extracellular pressure on the coronary circulation.

The coronary flow models are coupled to the cellular models via the wall shear stress terms, which regulate the endothelial cell function, resulting in altered hemodynamics (due to plaque growth) and wall remodeling (i.e., change in the wall elasticity).

Returning to FIG. 2, at step 210, hemodynamic quantities are determined based on the flow computations. Several indicators of coronary artery disease have been proposed. It has been shown that for artherosclerosis, the functional rather than morphological aspects of a stenosis are able to predict patient outcome. The functional aspects are related to the blood flow rate through a stenosis, during rest and hyperemic state. The morphological aspects are related to the geometrical shape of the stenosis and can be determined through quantitative coronary angiography (QCA). There are various reasons why the geometrical shape of the stenosis alone, cannot predict patient outcome. For example, QCA is 2D representation, hence the diameter reduction cannot be determined exactly, and in the case of diffuse disease, it is difficult to determine the reference diameter. Also, a previous myocardial infarct can decrease the significance of the stenosis if the area to be supplied has been affected by the infarct. Further, collateral blood flow can increase flow and attenuate the effect of the stenosis. The functional significance is determined through different indicators such as, trans-stenotic pressure drop, coronary flow reserve (CFR), relative flow reserve (RFR) or fractional flow reserve (FFR). FFR offers a series of advantages over the others indicators. For example, FFR does not include the rest state (which is highly dependent on the hemodynamic parameters), it does not depend on the existence of an adjacent healthy vessel (as opposed to RFR, hence it can be applied in case of multivessel disease), and it includes the effect of collateral flow and of previous myocardial infarct. Also, it has been shown that FFR is highly independent of the hemodynamic condition of the patient (blood pressure, heart rate, contractility). FFR is calculated by dividing the pressure distal to the stenosis to the pressure proximal to a stenosis. Since venous pressure can be generally taken as equal to zero without introducing a significant error, and the microvascular resistance is minimal and constant during hyperemic state for both a normal and stenotic vessel, the fraction of the pressures also represents the fraction of the normal maximum hyperemic flow that can still be supplied in the presence of the stenosis. Several studies have shown that a cut-off value of around 0.75 predicts if reversible ischemia is inducible in the myocardial region supplied by the stenosed vessel.

In an embodiment of the present invention, the patient-specific multi-scale model of the coronary circulation is used to determine functional parameters such as FFR for each stenosis, and thus to determine the functional significance for each stenosis.

Returning to FIG. 2, at step 212, simulations are performed for virtual intervention planning and decision support. For the diagnosis and management of coronary artery disease, the current clinical practice involves assessment of the diseased vessel by Quantitative Coronary Angiography (QCA). Such an assessment provides the clinician with a rich anatomical overview of the stenosis segment, including the area reduction, but does not provide a functional assessment. FFR values measured by invasively introducing a pressure wire in the stenosed vessel is the conventional technique for the functional assessment of the stenosis. QCA only evaluates the morphological significance of the stenosis and has a series of other limitations, and pressure-wire based FFR measurement involves risks associated with the intervention and for very narrow stenoses the pressure wire may induce an additional pressure drop.

All of these shortcomings are eliminated by the multi-scale coronary circulation modeling approach described herein. Previous CFD-based computations of the coronary tree have used exclusively 3D modeling, thus leading to high computational complexities, coupled with simple heart models, which cannot include all patient-specific aspects like local movement of the heart. Other approaches have included only 1D modeling (also coupled with a simple heart model), leading to difficulties in assessing the pressure-drop along the stenosis, since the exact shape of the stenosis is not considered.

After determining the functional significance of epicardial stenosis (in step 210), the proposed models can then be used to simulate the effect of different interventions (FIG. 13), which may be used improve the health state of the patient. Balloon inflation can be modeled by virtually reducing the obstruction from the stenosis and re-simulating the blood flow in the stenosis. In practice, when balloon inflation does not lead to satisfactory results (i.e., the trans-stenotic pressure drop remains high), stents are implanted. Virtual stent implantation with stents from different manufacturers can be implemented by adding a virtual model of a particular stent to the stenosis model, followed by performing the coupled flow analysis will enable the effects of the stent on wave propagation inside the arterial tree, and the impact of the stent on the hemodynamic variables to be analyzed.

In case of diffuse artherosclerotic disease, neither angioplasty, nor stent implants can improve the state of the patient and coronary artery bypass grafting (CABG) is typically performed. The introduction of such adjacent vessels, using various start and end points, can be simulated inside the multi-scale coronary circulation model in order to simulate CABG. Accordingly, the most suitable intervention or treatment option can be determined and the intervention or treatment can be planned (e.g., selecting the type of stent or the start and end points for CABG) prior to the performing the intervention.

Figure 9:
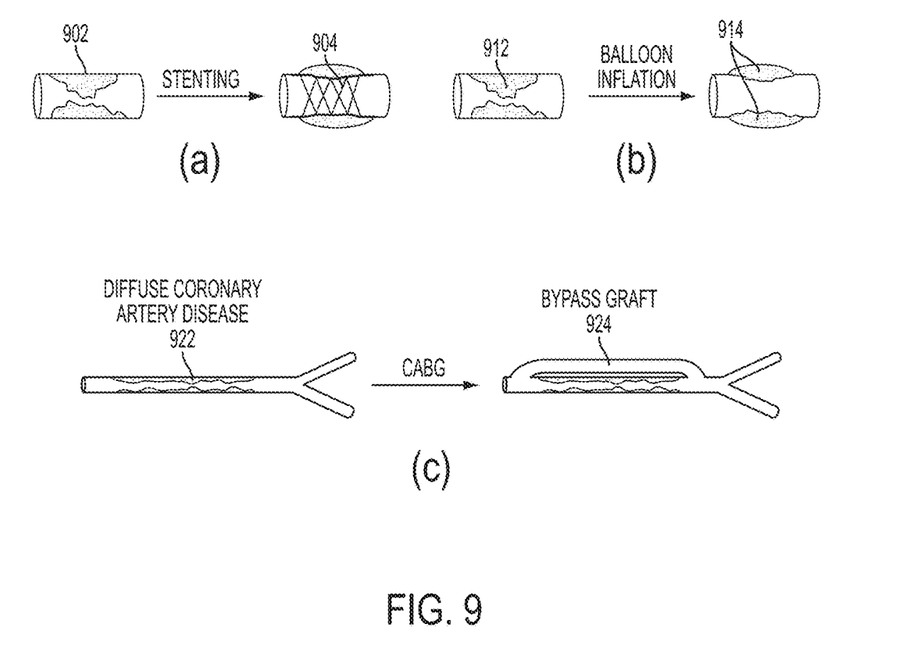
FIG. 9 illustrates examples of virtual intervention planning.

FIG. 9 illustrates examples of virtual intervention planning. As illustrated in FIG. 9, image (a) shows simulation of stent implantation in a stenosis region 902 using a virtual stent model 904. Image (b) shows simulation of balloon inflation inside a stenosis region 912 by simulating a reduced blockage 914. Image (c) shows simulation of CABG in a region 922 of a coronary artery having diffuse coronary artery disease by adding a virtual bypass graft vessel 924.

Figure 10:
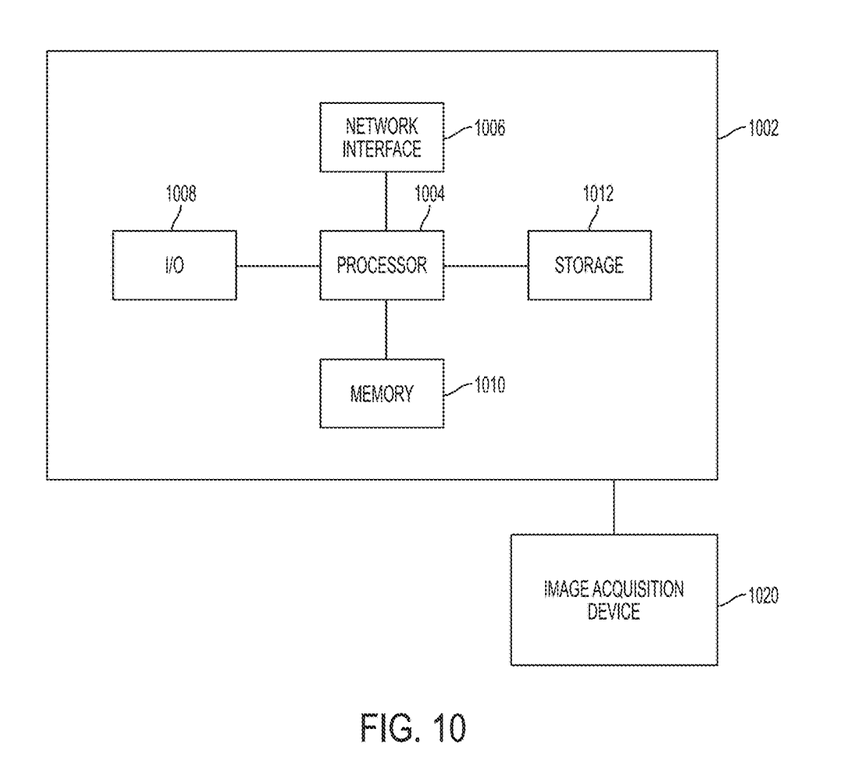
FIG. 10 is a high-level block diagram of a computer capable of implementing the present invention.

The above-described methods for multi-scale anatomical and functional modeling of coronary circulation using medical image data may be implemented on a computer using well-known computer processors, memory units, storage devices, computer software, and other components. A high-level block diagram of such a computer is illustrated in FIG. 10. Computer 1002 contains a processor 1004, which controls the overall operation of the computer 1002 by executing computer program instructions which define such operation. The computer program instructions may be stored in a storage device 1012 (e.g., magnetic disk) and loaded into memory 1010 when execution of the computer program instructions is desired. Thus, the steps of the methods of FIG. 2 may be defined by the computer program instructions stored in the memory 1010 and/or storage 1012 and controlled by the processor 1004 executing the computer program instructions. An image acquisition device 1020, such as a CT scanning device, MR scanning device, Ultrasound device, etc., can be connected to the computer 1002 to input image data to the computer 1002. It is possible to implement the image acquisition device 1020 and the computer 1002 as one device. It is also possible that the image acquisition device 1020 and the computer 1002 communicate wirelessly through a network. The computer 1002 also includes one or more network interfaces 1006 for communicating with other devices via a network. The computer 1002 also includes other input/output devices 1008 that enable user interaction with the computer 1002 (e.g., display, keyboard, mouse, speakers, buttons, etc.). Such input/output devices 1008 may be used in conjunction with a set of computer programs as an annotation tool to annotate volumes received from the image acquisition device 1020. One skilled in the art will recognize that an implementation of an actual computer could contain other components as well, and that FIG. 10 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method, comprising:
generating a patient-specific anatomical model of coronary arteries and a heart from medical image data of a patient;
generating a multi-scale functional model of coronary circulation based on the patient-specific anatomical model;
coupling, to the multi-scale functional model of coronary circulation, a cellular model of endothelial cell function that simulates changes in a mechanical property of a vascular wall due to a response of endothelial cells to hemodynamic forces, wherein a wall shear-stress value calculated by the multi-scale functional model of coronary circulation is used to couple the multi-scale functional model of coronary circulation to the cellular model of endothelial function through a mechanotransduction model; and
simulating blood flow in at least one stenosis region of at least one coronary artery and changes in a mechanical property of a vascular wall in the at least one stenosis region of the at least one coronary artery due to a response of endothelial cells in the vascular wall to hemodynamic forces from the simulated blood flow using the multi-scale functional model of coronary circulation and the cellular model of endothelial cell function coupled to the multi-scale functional model of coronary circulation.

2. The method of claim 1, wherein generating a patient-specific
anatomical model of coronary arteries and the heart from medical image
data of a patient comprises:
generating a 4D geometric model of the coronary arteries from 4D medical image data; and
generating a 4D anatomical model of the heart from the 4D medical image data.

3. The method of claim 2, wherein generating a 4D geometric model of the coronary arteries from 4D medical image data comprises:
segmenting the coronary arteries in each of a plurality of frames of the 4D medical image data; and
generating a geometric surface model for the segmented coronary arteries in each of the plurality of frames of the 4D medical image data.

4. The method of claim 2, wherein generating a 4D anatomical model of the heart from the 4D medical image data comprises:

extracting individual models of each of a plurality of heart components in each of a plurality of frames of the 4D medical image data; and integrating the individual models for the plurality of heart components in each of the plurality of frames of the 4D medical image data by establishing mesh point correspondence between the individual models.

5. The method of claim 1, wherein generating a multi-scale functional model of coronary circulation based on the patient-specific anatomical model comprises:

generating a 3D computation model for each of one or more stenosis regions in the coronary arteries;

generating 1D computation models for non-stenosis regions of the coronary arteries and the aorta; and representing microvasculature vessels using 0D lumped models.

6. The method of claim 5, wherein the 3D computation model for each stenosis region is a rigid wall 3D model and 0D interface models between the 3D computation model for each stenosis region and the 1D computation models for non-stenosis regions of the coronary arteries adjacent to each stenosis region concentrate compliance of the stenosis region.

7. The method of claim 5, wherein generating a multi-scale functional model of coronary circulation based on the patient-specific anatomical model further comprises:

generating a structured tree model for the vascular tree of the patient.

8. The method of claim 5, wherein generating a multi-scale functional model of coronary circulation based on the patient-specific anatomical model further comprises:

generating a reduced order model of the heart from full-order anatomical and hemodynamic models of the heart.

9. The method of claim 8, wherein generating a reduced order model of the heart from full-order anatomical and hemodynamic models of the heart comprises:

estimating motion and mechanical parameters of one or more heart components based on the anatomical and hemodynamic models of the heart; and determining boundary conditions for computational fluid dynamic simulations based on the motion and mechanical parameters of the one or more heart components.

10. The method of claim 1, wherein simulating blood flow in at least one stenosis region of at least one coronary artery comprises:

simulating blood flow in the at least one stenosis region using the multi-scale function model of coronary circulation based on boundary conditions determined from the anatomical model of the coronary arteries and the heart.

11. The method of claim 5, wherein simulating blood flow in at least one stenosis region of at least one coronary artery comprises:

performing computational fluid dynamics (CFD) simulations in the 3D computation model for each stenosis region and the 1D computation models; and coupling the 3D computation model for each stenosis region, the 1D computation models, and the 0D lumped models.

12. The method of claim 11, wherein coupling the 3D computation model for each stenosis region, the 1D computation models, and the 0D lumped models comprises:

deriving an inflow boundary condition of a system tree model by coupling a 1D computation model representing the aorta to the left ventricle of a heart model.

13. The method of claim 11, wherein coupling the 3D computation model for each stenosis region, the 1D computation models, and the 0D lumped models comprises:

imposing boundary conditions representing an influence of heart contractions on 1D computation models of epicardial coronary vessels using a 3D strain map extracted from the medical image data.

14. The method of claim 11, wherein coupling the 3D computation model for each stenosis region, the 1D computation models, and the 0D lumped models comprises:

determining extracellular pressure applied to the 1D computation models of coronary vessels based on locations of the coronary vessels using the 0D lumped models.

15. The method of claim 11, wherein coupling the 3D computation model for each stenosis region, the 1D computation models, and the 0D lumped models comprises:

coupling the 1D computation models to the 0D lumped models via wall shear stress terms.

16. The method of claim 11, wherein coupling the 3D computation model for each stenosis region, the 1D computation models, and the 0D lumped models comprises:

coupling the 3D computation model to adjacent 1D computation models using 0D interface models.

17. The method of claim 1, further comprising:

calculating a hemodynamic quantity to determine a functional significance of the at least one stenosis region based on the simulated blood flow through the at least one stenosis region.

18. The method of claim 17, wherein calculating a hemodynamic quantity to determine a functional significance of the at least one stenosis region based on the simulated blood flow through the at least one stenosis region comprises:

calculating a fractional flow reserve (FFR) of the at least one stenosis region based on the computation blood flow through the at least one stenosis region.

19. The method of claim 1, further comprising:

simulating a virtual intervention in at least one stenosis region using the multi-scale function model of coronary circulation.

20. The method of claim 19, wherein simulating a virtual intervention in at least one stenosis region using the multi-scale function model of coronary circulation comprises:

simulating a balloon inflation by virtually reducing an obstruction from the at least one stenosis region in the multi-scale function model of coronary circulation and re-simulating the blood flow through the at least one stenosis region.

21. The method of claim 19, wherein simulating a virtual intervention in at least one stenosis region using the multi-scale function model of coronary circulation comprises:

simulating a stent implantation by introducing a virtual stent model to at least one stenosis region in the multi-scale function model of coronary circulation and re-simulating the blood flow through the at least one stenosis region.

22. The method of claim 19, wherein simulating a virtual intervention in at least one stenosis region using the multi-scale function model of coronary circulation comprises:

simulating a coronary artery bypass graft (CABG) by adding a bypass vessel adjacent to the at least one stenosis region in the multi-scale function model of coronary circulation and re-simulating the blood flow through the at least one stenosis region.

23. An apparatus comprising:
a processor; and a memory storing computer program instructions, which when executed by the processor cause the processor to perform operations comprising:
generating a patient-specific anatomical model of coronary arteries and a heart from medical image data of a patient;
generating a multi-scale functional model of coronary circulation based on the patient-specific anatomical model;
coupling, to the multi-scale functional model of coronary circulation, a cellular model of endothelial cell function that simulates changes in a mechanical property of a vascular wall due to a response of endothelial cells to hemodynamic forces, wherein a wall shear-stress value calculated by the multi-scale functional model of coronary circulation is used to couple the multi-scale functional model of coronary circulation to the cellular model of endothelial function through a mechanotransduction model; and
simulating blood flow in at least one stenosis region of at least one coronary artery and changes in a mechanical property of a vascular wall in the at least one stenosis region of the at least one coronary artery due to a response of endothelial cells in the vascular wall to hemodynamic forces from the simulated blood flow using the multi-scale functional model of coronary circulation and the cellular model of endothelial cell function coupled to the multi-scale functional model of coronary circulation.

24. The apparatus of claim 23, wherein generating a patient-specific anatomical model of coronary arteries and the heart from medical image data of a patient comprises:
generating a 4D geometric model of the coronary arteries from 4D medical image data; and
generating a 4D anatomical model of the heart from the 4D medical image data.

25. The apparatus of claim 23, wherein generating a multi-scale functional model of coronary circulation based on the patient-specific anatomical model comprises:
generating a 3D computation model for each of one or more stenosis regions in the coronary arteries;
generating 1D computation models for non-stenosis regions of the coronary arteries and the aorta; and
representing microvasculature vessels using 0D lumped models.

26. The apparatus of claim 25, wherein the 3D computation model for each stenosis region is a rigid wall 3D model and 0D interface models between the 3D computation model for each stenosis region and the 1D computation models for non-stenosis regions of the coronary arteries adjacent to each stenosis region concentrate compliance of the stenosis region.

27. The apparatus of claim 25, wherein generating a multi-scale functional model of coronary circulation based on the patient-specific anatomical model further comprises:
generating a reduced order model of the heart from full-order anatomical and hemodynamic models of the heart.

28. The apparatus of claim 23, wherein simulating blood flow in at least one stenosis region of at least one coronary artery comprises:
simulating blood flow in the at least one stenosis region using the multi-scale function model of coronary circulation based on boundary conditions determined from the anatomical model of the coronary arteries and the heart.

29. The apparatus of claim 25, wherein simulating blood flow in at least one stenosis region of at least one coronary artery comprises:
performing computational fluid dynamics (CFD) simulations in the 3D computation model for each stenosis region and the 1D computation models; and
coupling the 3D computation model for each stenosis region, the 1D computation models, and the 0D lumped models.

30. The apparatus of claim 23, wherein the operations further comprise:
calculating a hemodynamic quantity to determine a functional significance of the at least one stenosis region based on the simulated blood flow through the at least one stenosis region.

31. The apparatus of claim 23, wherein the operations further comprise:
simulating a virtual intervention in at least one stenosis region using the multi-scale function model of coronary circulation.

32. A non-transitory computer readable medium storing computer program instructions, which when operated on a processor cause the processor to perform operations comprising:
generating a patient-specific anatomical model of coronary arteries and a heart from medical image data of a patient;
generating a multi-scale functional model of coronary circulation based on the patient-specific anatomical model;
coupling, to the multi-scale functional model of coronary circulation, a cellular model of endothelial cell function that simulates changes in a mechanical property of a vascular wall due to a response of endothelial cells to hemodynamic forces, wherein a wall shear-stress value calculated by the multi-scale functional model of coronary circulation is used to couple the multi-scale functional model of coronary circulation to the cellular model of endothelial function through a mechanotransduction model; and
simulating blood flow in at least one stenosis region of at least one coronary artery and changes in a mechanical property of a vascular wall in the at least one stenosis region of the at least one coronary artery due to a response of endothelial cells in the vascular wall to hemodynamic forces from the simulated blood flow using the multi-scale functional model of coronary circulation and the cellular model of endothelial cell function coupled to the multi-scale functional model of coronary circulation.

33. The non-transitory computer readable medium of claim 32, wherein generating a patient-specific anatomical model of coronary arteries and the heart from medical image data of a patient comprises:
generating a 4D geometric model of the coronary arteries from 4D medical image data; and
generating a 4D anatomical model of the heart from the 4D medical image data.

34. The non-transitory computer readable medium of claim 32, wherein generating a multi-scale functional model of coronary circulation based on the patient-specific anatomical model comprises:
generating a 3D computation model for each of one or more stenosis regions in the coronary arteries;
generating 1D computation models for non-stenosis regions of the coronary arteries and the aorta; and representing microvasculature vessels using 0D lumped models.

35. The non-transitory computer readable medium of claim 34, wherein the 3D computation model for each stenosis region is a rigid wall 3D model and 0D interface models between the 3D computation model for each stenosis region and the 1D computation models for non-stenosis regions of the coronary arteries adjacent to each stenosis region concentrate compliance of the stenosis region.

36. The non-transitory computer readable medium of claim 34, wherein generating a multi-scale functional model of coronary circulation based on the patient-specific anatomical model further comprises:
  generating a reduced order model of the heart from full-order anatomical and hemodynamic models of the heart.

37. The non-transitory computer readable medium of claim 32, wherein simulating blood flow in at least one stenosis region of at least one coronary artery comprises:
  simulating blood flow in the at least one stenosis region using the multi-scale function model of coronary circulation based on boundary conditions determined from the anatomical model of the coronary arteries and the heart.

38. The non-transitory computer readable medium of claim 34, wherein simulating blood flow in at least one stenosis region of at least one coronary artery comprises:
  performing computational fluid dynamics (CFD) simulations in the 3D computation model for each stenosis region and the 1D computation models; and
  coupling the 3D computation model for each stenosis region, the 1D computation models, and the 0D lumped models.

39. The non-transitory computer readable medium of claim 32, the operations further comprising:
  calculating a hemodynamic quantity to determine a functional significance of the at least one stenosis region based on the simulated blood flow through the at least one stenosis region.

40. The non-transitory computer readable medium of claim 32, the operations further comprising:
  simulating a virtual intervention in at least one stenosis region using the multi-scale function model of coronary circulation.

41. The method of claim 1, further comprising:
  tracking initiation and subsequent growth of coronary plaques, and an effect of the coronary plaques on the coronary circulation based on simulations of blood flow in the coronary arteries and changes in the mechanical property of vascular walls of the coronary arteries due to a response of endothelial cells in the vascular walls to hemodynamic forces from the simulated blood flow using the multi-scale functional model of coronary circulation and the cellular model of endothelial cell function coupled to the multi-scale functional model of coronary circulation.

42. The method of claim 1, wherein simulating blood flow in at least one stenosis region of at least one coronary artery and changes in a mechanical property of a vascular wall in the at least one stenosis region of the at least one coronary artery due to a response of endothelial cells in the vascular wall to hemodynamic forces from the simulated blood flow using the multi-scale functional model of coronary circulation and the cellular model of endothelial cell function coupled to the multi-scale functional model of coronary circulation comprises:
  adjusting the simulated blood flow in the at least one stenosis region of the at least one coronary artery in response to the simulated changes in the mechanical property of the vascular wall in the at least one stenosis region of the at least one coronary artery.

43. The method of claim 1, wherein the cellular model of endothelial cell function performs a computer-based simulation of changes in a wall elasticity of a vascular wall due to a response of endothelial cells to hemodynamic forces, and simulating blood flow in at least one stenosis region of at least one coronary artery and changes in a mechanical property of a vascular wall in the at least one stenosis region of the at least one coronary artery due to a response of endothelial cells in the vascular wall to hemodynamic forces from the simulated blood flow using the multi-scale functional model of coronary circulation and the cellular model of endothelial cell function coupled to the multi-scale functional model of coronary circulation comprises:
  simulating changes in the wall elasticity of the vascular wall in the at least one stenosis region of the at least one coronary artery due to a response of endothelial cells in the vascular wall to hemodynamic forces using the cellular model of endothelial cell function coupled to the multi-scale functional model of coronary circulation.

* * * * *